United States Patent [19]

Simmons

[11] 4,073,626
[45] Feb. 14, 1978

[54] HYDROCARBON FUEL ADDITIVE AND PROCESS OF IMPROVING HYDROCARBON FUEL COMBUSTION

[75] Inventor: Richard W. Simmons, Bellingham, Wash.

[73] Assignee: Ferrous Corporation, Bellevue, Wash.

[21] Appl. No.: 641,647

[22] Filed: Dec. 17, 1975

Related U.S. Application Data

[63] Continuation of Ser. No. 461,877, April 18, 1974, abandoned, which is a continuation of Ser. No. 798,182, Feb. 10, 1969, abandoned.

[51] Int. Cl.$^2$ ................................................ C10L 1/22
[52] U.S. Cl. .......................................... 44/57; 44/68; 44/72
[58] Field of Search ........................... 44/57, 68, 72

[56] References Cited

U.S. PATENT DOCUMENTS

| 1,820,983 | 9/1931 | Loomis | 44/72 |
| 3,282,858 | 11/1966 | Simmon et al. | 44/68 |

FOREIGN PATENT DOCUMENTS

| 491,648 | 9/1938 | United Kingdom | 44/57 |

*Primary Examiner*—Daniel E. Wyman
*Assistant Examiner*—Mrs. Y. Harris-Smith
*Attorney, Agent, or Firm*—Seed, Berry, Vernon & Baynham

[57] ABSTRACT

An improved liquid diesel fuel for diesel engines is made by incorporating at least 0.003% by weight of a mixture of an iron salt of an aromatic nitro acid and a nitroaliphatic compound having one to four carbon atoms, into the diesel fuel. The weight ratio of the aromatic nitro acid salt to the nitroaliphatic compound ranges from 1:10 to 1:100. The additive, when added to diesel fuel, (1) substantially eliminates hard carbon deposits from the valve and exhaust systems of diesel engines, thereby improving the efficiency of the engines and decreasing overhaul expense, (2) reduces air pollutants such as oxides of sulphur and nitrogen, and virtually eliminates carbon monoxide from diesel exhausts and (3) reduces or substantially eliminates slime deposits which form during diesel fuel storage.

9 Claims, No Drawings

HYDROCARBON FUEL ADDITIVE AND PROCESS OF IMPROVING HYDROCARBON FUEL COMBUSTION

This is a continuation of application Ser. No. 461,877, filed Apr. 18, 1974, now abandoned, which is a continuation of Ser. No. 798,182 filed Feb. 10, 1969 now abandoned.

BACKGROUND OF THE INVENTION

1. Field of the Invention

This invention relates to an improved liquid hydrocarbon diesel fuel and fuel additive for diesel engine fuel, and to a process of reducing air pollutants, hard carbon deposits in diesel engines and slime deposits in diesel fuel during storage.

2. Prior Art Relating to the Disclosure

A fuel additive comprising an aromatic metal free nitro compound such as picric acid and an iron salt of aromatic nitro acid such as ferrous picrate, dissolved in a solvent as methylated spirits of benzene, is disclosed in U.S. Pat. No. 2,506,539. This additive has several disadvantages which prevent its wide use. It has a very low flash point, is highly corrosive and is unstable. An attempt to overcome certain of these disadvantages is disclosed in U.S. Pat. No. 3,282,858 by the use of non-oxidizing compatible solvents for the aromatic metal free nitro compound and iron salts of the aromatic nitro acid. While this has been partially successful, the improved additive of this invention is much preferred.

In heavy duty diesel engines, such as those used in ships, locomotives, trucks and power generators, the combination of long idling times, variable fuel composition and frequent acceleration loads make the engine designer's work very difficult. He must compromise on several ideal designs and evolve a system which works adequately over a variety of operating conditions. When fuel is burned, several processes occur. At least three of these are important: (1) the ratio of air to fuel, (2) the degree of mixing at any particular place in the flame, and (3) the temperature. Depending on these three variables, the fuel may be either oxidized, cracked, or discharged unburned. Where there is an adequate supply of well-mixed air, oxygen is added to the fuel vapors producing successively more and more oxidized compound until the final state of minimum energy — carbon dioxide and water — is attained. If, on the other hand, there is not enough air to support this process in the reducing zone of the flame, the fuel breaks down as a result of the heat into smaller molecular units. This is the so-called cracking process which must occur with heavier types of fuel in order that they may become gases. However, if smaller units, ultimately carbon, slip through the visible flame zone, they are exhausted, giving a smoky exhaust containing carbon and smog-producing unburned hydrocarbons. Therefore, good mixing and atomization of the right portion of fuel and air with adequate heat present is vitally important. The additive of this invention improves the fuel combustion process in that it (1) improves fuel-air ratios by vigorously separating fuel droplets, giving far superior carburetion; (2) reduces or eliminates carbon deposits by more complete combustion; (3) promotes normal combustion chamber temperatures by removing heat-insulating carbon deposits by allowing more rapid cooling; (4) restores compression ratios as closely as possible to the engine's design allowing for normal motor wear; (5) reduces drastically crank case contamination by carbon, gum and varnish, giving longer oil life; (6) allows acids and other impurities to be more easily exhausted by reducing varnish, gum and carbon as binders; (7) reduces or eliminates injector fouling; (8) reduces piston ring and valve sticking; (9) increases horsepower; (10) achieves easier starting, smoother operation and faster pickup; (11) reduces or eliminates sparks from the exhaust; (12) reduces exhaust gas odors to non-objectionable levels; and (13) reduces air pollutants.

SUMMARY OF THE INVENTION

One of the main objects of this invention is an improved additive for liquid hydrocarbon fuels, particularly diesel fuel, the additive having the effect of reducing and, in many cases, eliminating hard carbon deposits, exhaust sparks and exhaust pollutants from the exhausts of these engines.

Another object is an improved additive which is non-corrosive, stable, and low in cost for improving diesel fuel.

A further object is the reduction and substantial eliminations of slime deposits which form in diesel fuel during storage.

A further object of this invention is in the reduction of the frequency of overhaul for removal of hard carbon deposits which accumulate during burning of conventional diesel fuel.

These and other objects are accomplished by metering into the fuel controlled amounts of a mixture of an iron salt of an aromatic nitro acid and a nitroaliphatic compound having from one to four carbon atoms. The amount of additive used should be sufficient to insure that the exhaust gases of the burned fuel contain a useful amount of atomically dispersed iron which catalyzes the residual combustion of the primary exhaust through the hot exhaust areas. Preferably, the additive is a mixture of ferrous picrate and a nitroaliphatic compound dissolved in a compatible solvent.

DETAILED DISCLOSURE OF THE INVENTION

The fuel additive of this invention is a solution of preferably, ferrous picrate and nitroaliphatic compound in a blend of solvents and oil to which antioxidants, corrosion inhibitors and discosity regulating materials may be added. When this mixture is added to diesel engine fuel in the recommended quantities, its active ingredients decompose during the first stages of combustion to increase turbulent mixing within the combustion chamber. Oxygen is transferred to the fuel and gases at an accelerated rate creating more complete oxidation in the short time allowed by the firing cycle. In heavy duty diesel engines, there is a tendency for hard carbon deposits to develop in the exhaust ports and valves. The carbon build-up in the valves prevents complete closing of the valves which naturally lowers the efficiency of the engine. Hard carbon deposits also build up on the piston dome or cylinder head of diesel engines. A frequently observed condition is rough idling caused by a flash firing, the likely cause of this imperfection being the presence of these carbon deposits. The fuel additive of this invention removes existing carbon deposits in the exhaust system. With the elimination of exhaust stack carbon, the burning sparks from the stacks are no longer a source of concern. With complete combustion, these are eliminated, assuring safety for tarp covered loads, powered vehicles and equipment operating in dry timber or grass covered terrain.

The weight ratio of the iron salt of the aromatic nitro acid and nitroaliphatic compound may vary from 1:10 to 1:100, although preferably a weight ratio of from 1:15 to 1:55 aromatic nitro acid to nitroaliphatic compound is used.

The amount of the additive added to the liquid hydrocarbon fuel is relatively small. Results can be obtained using as little as 0.003% of the mixture based on the fuel weight. Amounts up to 0.03% or greater can be used if desired. Amounts greater than 0.006%, however, are of no particular advantage. Use of a large excess, while not detrimental to the engine in which the fuel is combusted, does affect the calorific value of the fuel.

The aromatic nitro acid salt which is preferably used in this invention is ferrous picrate, although ferrous and ferric salts of trinitrophenols, trinitrocresols and picramic acid can be used. The nitroaliphatic compounds useful in this invention are those containing one nitro group and from one to four carbon atoms, such as nitromethane, nitroethane, the nitropropanes and nitrobutanes. Preferably 1-nitropropane is used, although satisfactory results can be obtained with any of the above-mentioned compounds.

The additive is usually added to the liquid hydrocarbon fuel in a solvent. As small amounts of the iron salt and nitroaliphatic compound are added to the fuel, they are usually dissolved together in a suitable organic solvent which is compatible with the additive components and the hydrocarbon fuel. Such solvents include, for example, toluene, xylene, isopropyl alcohol, butanol, mineral oil, fusel oil and aromatic petroleum fractions.

Unexpectedly, it was found that the fuel additive of this invention has the effect of reducing or substantially eliminating slime deposits which invariably form during storage of diesel fuel. These slimes are caused by the growth of bacteria and fungi whose habitat is within drops or pools of condensed water upon which the fuel is floating and whose energy source is the fuel itself. The results of slime contamination are corrosion of the tank metal and fouling of lines, screens, etc., with the sheer bulk of the slime which comprises these organisms. The composition of this invention, added in the same amounts used for improving fuel performance, has also been found to effectively control and eliminate slime deposits.

The following examples are exemplary only and are not intended to be limiting in any manner.

EXAMPLE 1

The fuel additive of this invention was prepared by dissolving 220 grams of coperas (FeSO4.7H$_2$O) in four liters of hot water (70° C.) containing 0.5% hydroquinone. To this solution was then added 70 grams anhydrous sodium carbonate. The mixture was stirred and the precipitated ferrous carbonate allowed to settle out. The relatively clear aqueous layer was decanted off and the precipitate washed with additional hot water. After washing with water, the precipitate was washed with denatured alcohol. The mixture was then dispersed in isopropyl alcohol and 400 grams picric acid added. The mixture was stirred and allowed to react for several hours until evolution of carbon dioxide was completed. Then 1100 grams of 1-nitropropane was added and the mixture dissolved in 20 gallons isopropyl alcohol and 78 gallons of Pacific base oil. The product was ready for packaging in drums or cans.

EXAMPLE 2

A transit coach, powered by a 202 horsepower diesel engine was processed by feeding the additive of Example 1 in the fuel intake line such that with each 100 gallons of incoming fuel, there were mixed 0.6 grams of ferrous picrate and 19.2 grams of 1-nitropropane or approximately 0.005% by weight of the mixture based on the fuel. Table I shows the exhaust gas analysis at the start of the test and one month later.

TABLE I

|  | Start | One Month | % reduction |
| --- | --- | --- | --- |
| Oxides of Nitrogen | 125 ppm | 55 ppm | 56% |
| Sulfur dioxide | 15 ppm | 4 ppm | 73% |
| Carbon monoxide | 150 ppm | 12.5 ppm | 91.6% |

The skilled technician who took the examples noted that the typical exhaust odor of the diesel bus was markedly reduced by the end of the month.

EXAMPLE 3

A tow boat, hauling barges to Alaska from Seattle, was processed by adding directly to the fuel tank in measured quantities approximately 0.005% by weight, based on the fuel, of the concentrate of Example 1. On previous runs, prior to being treated with the liquid additive, it had been necessary to lift the engine head, chip out hard carbon deposits and free the piston rings on each return to Seattle. After addition of the fuel additive and after a run between Seattle and Alaska and return, the head was lifted and found to be free of hard carbon deposits and the rings were loose. An appreciable saving in fuel and lubricating oil was logged for the trip.

EXAMPLE 4

A railway locomotive whose power plant was a two cycle opposed piston diesel engine, was fitted with a concentrate supply tank, which fed to a venturi-type meter installed in the fuel intake line. The meter was so constructed that for each 100 gallons of incoming fuel there was charged and mixed 0.6 grams of ferrous picrate and 19.2 grams of 1-nitropropane or approximately 0.005% by weight of ferrous picrate and 1-nitropropane based on the weight of the fuel. This engine was coupled randomly with three other engines and placed in daily service, round trip, between Seattle, Washington, and Portland, Oregon.

Observers reported that sparks from the two untreated engines drifted back three cars while the sparks from the treated locomotive were so negligible as to be barely seen within a few feet of the stack. After approximately one month of service, the locomotive was taken to the shop and the head pulled. Instead of the expected hard carbon deposits which ordinarily require two or three days of heavy tooling, there were minor amounts of carbon which could be wiped off with a rag, or blown off with a steam cleaner.

Exhaust analyses for the engine just described are shown in Table 2 along with parallel samples of an untreated locomotive with the same time from overhaul. Each engine was operated on a dynamometer and the data measured at idle, half-throttle and full-throttle.

In addition, exhaust analyses for a second treated and untreated pair of locomotives are given, the method of treating being similar to that described above.

Since the test was made on stationary equipment, it was possible to measure the circles of carbon which settled around each stack. The stack of treated engine A was coated with carbon for approximately one foot each way from the stacks while the untreated engine B was coated with the carbon for approximately three feet each way from the stacks.

During the period of time which the additive was being fed into the diesel fuel, there was no need to add an additional sterilant to the fuel. No indication of algae or fungus was found in the fuel filters.

It can be seen from the above examples that the fuel additive of this invention, when added to diesel fuel, results in a distinct number of advantages outlined previously.

2. The fuel according to claim 1 wherein the iron salt of the aromatic nitro acid is ferrous picrate.

3. The fuel according to claim 2 wherein the nitroaliphatic compound in nitropropane.

4. The fuel according to claim 3 wherein at least 0.004% by weight of a mixture of ferrous picrate and nitropropane is added, the ratio of ferrous picrate to nitropropane ranging from 1:15 to 1:55.

5. An improved additive for diesel fuel comprising a mixture of from one part by weight of an iron salt of an aromatic nitro acid to 10 to 100 parts by weight of a nitroaliphatic compound having from one to four carbon atoms.

6. The additive of claim 5 wherein the iron salt of the aromatic nitro acid is ferrous picrate.

TABLE II

| IDLE | Engine A (treated) | Engine B (untreated) | % Reduction | Engine C (treated) | Engine D (untreated) | % Reduction |
|---|---|---|---|---|---|---|
| Carbon Monoxide | 55 ppm | 100 ppm | 45% | 10 ppm | 100 ppm | 90% |
| Oxides of Nitrogen | 138 ppm | 2000 ppm | 93% | 15 ppm | 50 ppm | 73% |
| Sulfur Dioxide | 5 ppm | 11 ppm | 54% | 5 ppm | 5 ppm | 20% |
| Carbon Dioxide | 0.6 % | 1.3 % | 54% | 0 | 0 | — |
| Heavy Hydrocarbons | 12 ppm | 25 ppm | 52% | 7 ppm | 5 ppm | (28%) |
| HALF THROTTLE | | | | | | |
| Carbon Monoxide | 25 ppm | 100 ppm | 75% | 10 ppm | 350 ppm | 96.6% |
| Oxides of Nitrogen | — — | 1050 ppm | — | 5 ppm | 10,000 ppm | 99.5% |
| Sulfur Dioxide | 5 ppm | 15 ppm | 67% | 1 ppm | 25 ppm | 96 % |
| Carbon Dioxide | 1.9 % | 3.8 % | 50% | 1.5 % | — — | — |
| Heavy Hydrocarbons | 14 ppm | 17 ppm | 18% | 12 ppm | — — | — |
| FULL THROTTLE | | | | | | |
| Carbon Monoxide | 25 ppm | 8000 ppm | 99% | 250 ppm | 15,000 ppm | 98.1% |
| Oxides of Nitrogen | 8000 ppm | 25,000 ppm | 68% | 4000 ppm | 20,000 ppm | 80 % |
| Sulfur Dioxide | 10 ppm | 200 ppm | 95% | 40 ppm | 40 ppm | — |
| Carbon Dioxide | 1.7 % | 5.2 % | 67% | 3 % | 4 % | (25%) |
| Heavy Hydrocarbons | 25 ppm | 22 ppm | 13.7% more | 10 ppm | 15 ppm | — |
| HORSEPOWER | | | | | | |
| Half Throttle | 768 | 686 | 11.9% more | 457.6 | 328.4 | 39.5% more |
| Full Throttle | 1728 | 1632 | 5.9% more | 1445 | 1312.4 | 10 % more |

The embodiments of the invention in which an exclusive property or privilege is claimed are defined as follows:

1. An improved liquid hydrocarbon fuel containing at least 0.003% by weight of a mixture of an iron salt of an aromatic nitro acid and a nitroaliphatic compound having from one to four carbon atoms, the weight ratio of aromatic nitro acid to nitroaliphatic compound ranging from 1:10 to 1:100.

7. The additive of claim 6 wherein the nitroaliphatic compound is nitropropane.

8. The additive of claim 5, including a compatible solvent mixture of the mixture.

9. The additive of claim 8 wherein the solvent is one selected from the group consisting of isopropyl alcohol, butanol, toluene, xylene, mineral oil, fuel oil and aromatic petroleum fractions.

* * * * *